United States Patent
Kim et al.

(10) Patent No.: US 11,884,638 B2
(45) Date of Patent: Jan. 30, 2024

(54) COMPOUND OR SALT THEREOF, COMPOSITION FOR CYSTEINE DETECTION, FLUORESCENT PROBE AND COMPOSITION FOR DIAGNOSING CANCER CONTAINING THE SAME, METHOD FOR DETECTING CYSTEINE, METHOD FOR PROVIDING INFORMATION FOR DIAGNOSING CANCER, AND METHOD FOR PRODUCING COMPOUND

(71) Applicants: Industry-Academic Cooperation Group of Kyung Hee University, Yongin-si (KR); SEOUL NATIONAL UNIVERSITY HOSPITAL, Seoul (KR)

(72) Inventors: Do Kyoung Kim, Seoul (KR); Chang Wook Jeong, Seoul (KR); Jong Min An, Seoul (KR)

(73) Assignees: Industry-Academic Cooperation Group of Kyung Hee Universtiy and; SEOUL NATIONAL UNIVERSITY HOSPITAL

( * ) Notice: Subject to any disclaimer, the term of this patent is extended or adjusted under 35 U.S.C. 154(b) by 50 days.

(21) Appl. No.: 17/512,820

(22) Filed: Oct. 28, 2021

(65) Prior Publication Data
US 2023/0105273 A1    Apr. 6, 2023

(30) Foreign Application Priority Data

Aug. 2, 2021 (KR) .................... 10-2021-0101171

(51) Int. Cl.
C07D 271/12 (2006.01)
G01N 33/574 (2006.01)
G01N 33/58 (2006.01)
G01N 33/68 (2006.01)

(52) U.S. Cl.
CPC ..... C07D 271/12 (2013.01); G01N 33/57411 (2013.01); G01N 33/57488 (2013.01); G01N 33/582 (2013.01); G01N 33/6815 (2013.01)

(58) Field of Classification Search
CPC .............................. C07D 271/12; G01N 33/582
See application file for complete search history.

(56) References Cited

U.S. PATENT DOCUMENTS 6,300,136 B1 * 10/2001 Koch ................... G01N 33/574
436/119

FOREIGN PATENT DOCUMENTS

CN      110927156 A  *  3/2020
KR    1020210098874 A     8/2021

OTHER PUBLICATIONS

An; Sensors and Actuators B: Chemical 2022, 360, 131646. https://doi.org/10.1016/j.snb.2022.131646 (Year: 2022).*
An; Chem. Sci., 2020, 11, 5658. https://doi.org/10.1039/D0SC01085E (Year: 2020).*
Chokchaichamnankit; Oncology Letters; 2019, 17, 5453-5468. https://doi.org/10.3892/ol.2019.10227 (Year: 2019).*
Duan; ChemistryOpen 2019, 8, 316-320. https://doi.org/10.1002/open.201900045 (Year: 2019).*
Hammers; Analytical Chemistry 2014, 86, 7135-7140. https://doi.org/10.1021/ac501680d (Year: 2014).*
Kessler; Bioorg. Med. Chem. Lett. 2013, 23, 5575-5577. https://doi.org/10.1016/j.bmcl.2013.08.048 (Year: 2013).*
Kim; Analytica Chimica Acta 2022, 1202, 339678. https://doi.org/10.1016/j.aca.2022.339678 (Year: 2022).*
Wang; Dyes and Pigments 2018, 158, 151-156. https://doi.org/10.1016/j.dyepig.2018.05.039 (Year: 2018).*
Chemical Abstracts STN Registry Database Record for RN 883224-92-8, 4-(4-Fluorophenoxy)-7-nitro-2,1,3-benzoxadiazole, Entered STN May 8, 2006. (Year: 2006).*
Goodman; Cancer 2000, 89, 376-382. https://doi.org/10.1002/1097-0142(20000715)89:2%3C376::AID-CNCR24%3E3.0.CO;2-O (Year: 2000).*
Liu; Sci Rep 2016, 6, 21433. https://doi.org/10.1038/srep21433 (Year: 2016).*
"A Fluorescent Turn-on Probe for the Visualization of Glioblastoma" JM An, et al., 2020.
"A Cysteine Selective Fluorescent Probe for Tumor Imaging" JM An, et al, 2020.

* cited by examiner

*Primary Examiner* — Daniel R Carcanague
(74) *Attorney, Agent, or Firm* — Maine Cernota & Curran (57) ABSTRACT

The present disclosure relates to a novel compound or a salt thereof, a composition for detecting cysteine, a fluorescent probe, and a composition for diagnosing cancer, which contain the same, a method for detecting cysteine, a method for providing information for diagnosing cancer, and a method for producing the novel compound. According to the present disclosure, there may be provided a method of synthesizing and purifying a fluorescent probe for cysteine detection and applying the same to diagnose cervical cancer by detecting cysteine in human urine.

3 Claims, 4 Drawing Sheets

COMPOUND OR SALT THEREOF, COMPOSITION FOR CYSTEINE DETECTION, FLUORESCENT PROBE AND COMPOSITION FOR DIAGNOSING CANCER CONTAINING THE SAME, METHOD FOR DETECTING CYSTEINE, METHOD FOR PROVIDING INFORMATION FOR DIAGNOSING CANCER, AND METHOD FOR PRODUCING COMPOUND

RELATED APPLICATIONS

This application claims priority under the Paris Convention to KR Application No. 10-2021-0101171, filed Aug. 2, 2021. This application is herein incorporated by reference, in its entirety, for all purposes.

FIELD OF THE INVENTION

The present disclosure relates to a novel compound or a salt thereof, a composition for detecting cysteine, a fluorescent probe, and a composition for diagnosing cancer, which contain the same, a method for detecting cysteine, a method for providing information for diagnosing cancer, and a method for producing the novel compound.

BACKGROUND OF THE INVENTION

Cervical cancer is a type of cancer that occurs in women, and refers to a collection of cancers that occurs in a woman from the vagina to the uterus. In particular, cervical cancer is a common type of cancer occurring in women (ranked fourth among all cancers), and since it is asymptomatic, the appropriate treatment period is missed and the majority of patients diagnosed with cervical cancer have a high mortality rate (in 2018, the number of patients diagnosed with cervical cancer was 570,000, and the number of deaths among the diagnosed patients was 311,000). Therefore, a system for diagnosing cervical cancer at an early stage and preventing cervical cancer is absolutely necessary worldwide.

Until now, technologies for detecting cervical cancer have been developed in various fields, but these technologies are so inefficient that they are not actually used in the medical field. In a diagnostic method that is used in the medical field, a subject is subjected to genetic testing using a polymerase chain reaction (PCR) for human papilloma virus (HPV), and when the subject belongs to a high-risk group, colposcopy and biopsy are performed.

However, this process requires a lot of time and money because it involves multiple processes rather than a single process. Thus, in order to reduce the consumption of time and money, it is required to develop a system for early diagnosis of cervical cancer.

Cysteine (CVS) is a representative amino acid having a thiol group and is involved in various biological processes. In particular, cysteine in cancer promotes tumor proliferation during oncogenesis.

Thus, it is important to develop a material that can selectively detect cysteine in vivo in the field of basic science, and selectively detecting cysteine using this technology and specifically detecting cysteine in specific intracellular organelles using this technology are variously applied to basic research as well as the understanding of cysteine-associated diseases.

In particular, in the field of cancer biology, the correlation between cysteine and cancer has been studied very importantly. Mass spectrometry, high-performance liquid chromatography (HPLC), cyclic voltammetry, capillary electrophoresis, etc. are known as methods for detecting the presence of cysteine in cells, but have disadvantages in that they not only require a complex analysis process, but also require a lot of time and money. In addition, it is impossible to detect cysteine in vivo in real time.

Analysis methods employing fluorescent molecular probes can overcome these shortcomings because they are simple and require little time and money. However, fluorescent molecular probes having a function of detecting cysteine, developed do date, have the disadvantage of having low selectivity to cysteine (CVS) due to the interference of homocysteine (HCy) and glutathione (GSH), and some fluorescent probes having selectivity to cysteine also exhibit their properties only under specific conditions.

For the selective detection of cysteine, a higher electrophilicity than those of other thiol groups and a specific steric effect than other thiol groups are required, and it is necessary to introduce concepts capable of inducing a fluorescent signal, such as intramolecular charge transfer (ICT), Forster resonance energy transfer (FRET), photoinduced proton transfer (PET), or excited-state intramolecular proton transfer (ESIPT).

However, selectively detecting only cysteine is still a very difficult task due to the structural similarity between cysteine and homocysteine.

Probes that emit strong fluorescence while having high selectivity and sensitivity to cysteine remain a very challenging task despite their importance, and the direct application of the presence of cysteine in materials derived from a human living body and cancer tissues has not yet been reported.

SUMMARY OF THE INVENTION

Accordingly, the present inventors have developed a breakthrough small molecular fluorescent probe which is produced by a simple and rapid synthesis method, shows high stability in vivo and in tissues, has low cytotoxicity, and emits fluorescence within a short time by interaction with cysteine in cells, tissues, and even human cancer tissues.

A fluorescent probe according to one embodiment of the present disclosure is capable of specifically detecting cysteine in the endoplasmic reticulum, which is a protein synthesis site in a cell. In addition, as this fluorescent probe has two-photon excitation properties, it has characteristics such as deep tissue permeability, low fluorescence interference from the tissue itself, high resolution, and low cell damage, and thus is applicable to two-photon microscopy-based bioimaging research.

According to one aspect of the present disclosure, there is provided a compound represented by the following Formula 1 or a salt thereof.

[Formula 1]

wherein: $X_1$ to $X_5$ are each independently hydrogen, deuterium, halogen, or a (C1-C6) alkyl group; at least one of $X_1$ to $X_5$ is a halogen; and Y is hydrogen, a (C1-C6) alkyl group, a (C2-C6) alkenyl group, a (C2-C6) alkynyl group, a (C1-C6) alkoxy group, a hydroxyl group, a hydroxyethyl group, an alkylamino group, a nitro group, a sulfonyl group, a sulfinyl group, a carboxyl group, a acetoxy group, a phenyl group, a (C7-C13) alkylphenyl group, a (C7-C13) alkylphenyloxy group, a (C8-C13) alkynylphenyl group, a (C8-C13) alkenylphenyl group, or a phenoxy group.

According to one embodiment of the present disclosure, $X_1$ to $X_5$ in Formula 1 are each a fluoro group, and Y is a nitro group.

According to another embodiment of the present disclosure, the compound emits fluorescence upon contact with cysteine.

According to still another embodiment of the present disclosure, the compound emits fluorescence when an ether bond in the compound is broken by cysteine.

According to yet another embodiment of the present disclosure, the compound reacts with cysteine in urine without reacting with other biomolecules in urine.

According to another aspect of the present disclosure, there is provided a composition for cysteine detection containing the compound represented by Formula 1 or a salt thereof.

According to one embodiment of the present disclosure, the composition emits fluorescence upon contact with cysteine.

According to another embodiment of the present disclosure, the composition further contains a solvent selected from among water, methanol, ethanol, isopropanol, n-propanol, n-butanol, isobutanol, t-butanol, acetone, isopropyl ether, acetonitrile, diethyl ether, tert-butylmethyl ether, and mixtures thereof.

According to still another aspect of the present disclosure, there is provided a fluorescent probe including the composition for cysteine detection.

According to yet another aspect of the present disclosure, there is provided a composition for diagnosing cancer containing the compound represented by Formula 1 or a salt thereof.

According to one embodiment of the present disclosure, the cancer is cervical cancer.

According to still yet another aspect of the present disclosure, there is provided a method for detecting cysteine, the method including steps of: bringing a composition containing the compound represented by Formula 1 or a salt thereof into contact with a sample containing cysteine; and checking fluorescence.

According to one embodiment of the present disclosure, the sample is a biological sample.

According to another embodiment of the present disclosure, the biological sample is urine.

According to still another embodiment of the present disclosure, 1 ng/μL or less of cysteine is detected.

According to a further aspect of the present disclosure, there is provided a method for providing information for diagnosing cancer, the method including a step of treating a sample with the compound represented by Formula 1 or a salt thereof.

According to one embodiment of the present disclosure, the cancer is cervical cancer.

According to another embodiment of the present disclosure, the sample is a biological sample.

According to still another embodiment of the present disclosure, the biological sample is urine.

According to another further aspect of the present disclosure, there is provided a method for producing the compound represented by Formula 1, the method including a step of allowing a compound represented by the following Formula 2 to react with a compound represented by the following Formula 3:

[Formula 2]

[Formula 3]

wherein: $X_1$ to $X_5$ are each independently hydrogen, deuterium, halogen, or a (C1-C6) alkyl group; at least one of $X_1$ to $X_5$ is a halogen; Hal is a halogen; and Y is hydrogen, a (C1-C6) alkyl group, a (C2-C6) alkenyl group, a (C2-C6) alkynyl group, a (C1-C6) alkoxy group, a hydroxyl group, a hydroxyethyl group, an alkylamino group, a nitro group, a sulfonyl group, a sulfinyl group, a carboxyl group, a acetoxy group, a phenyl group, a (C7-C13) alkylphenyl group, a (C7-C13) alkylphenyloxy group, a (C8-C13) alkynylphenyl group, a (C8-C13) alkenylphenyl group, or a phenoxy group.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

According to the present disclosure, there is provided a compound represented by the following Formula 1 or a salt thereof.

[Formula 1]

wherein: $X_1$ to $X_5$ are each independently hydrogen, deuterium, halogen, or a (C1-C6) alkyl group; at least one of $X_1$ to $X_5$ is a halogen; and Y is hydrogen, a (C1-C6) alkyl group, a (C2-C6) alkenyl group, a (C2-C6) alkynyl group, a (C1-C6) alkoxy group, a hydroxyl group, a hydroxyethyl group, an alkylamino group, a nitro group, a sulfonyl group, a sulfinyl group, a carboxyl group, a acetoxy group, a phenyl group, a (C7-C13) alkylphenyl group, a (C7-C13) alkylphenyloxy group, a (C8-C13) alkynylphenyl group, a (C8-C13) alkenylphenyl group, or a phenoxy group.

Specific examples of the halogen include a fluoro group, a chloro group, a bromo group, an iodo group, and the like.

Specific examples of the "(C1-C6) alkyl group" include a methyl group, an ethyl group, an n-propyl group, an isopropyl group, an n-butyl group, an isobutyl group, a tert-butyl group, and a sec-butyl group.

Specific examples of the "(C2-C6) alkenyl group" include a vinyl group, a 1-propenyl group, a 2-propenyl group, a 1-butenyl group, a 2-butenyl group, a 3-butenyl group, a 2-methylbut-2-enyl group, and the like.

Specific examples of the "(C2-C6) alkynyl group" include an ethynyl group, a 1-propynyl group, a 2-propynyl group, a 1-butynyl group, a 2-butynyl group, a 3-butynyl group, a 1-methylpent-2-ynyl group, and the like.

Specific examples of the "(C1-C6) alkoxy group" include a methoxy group, an ethoxy group, a propoxy group, a butoxy group, and the like.

According to one embodiment of the present disclosure, $X_1$ to $X_5$ may be each a fluoro group.

According to one embodiment of the present disclosure, Y may be a nitro group.

Specifically, the compound of Formula 1 may include a structure of 4-nitro-7-(perfluorophenoxy)benzo[c][1,2,5] oxadiazole.

The compound of Formula 1 emits a fluorescence signal when bound to cysteine.

Specifically, the compound of Formula 1 may emit a fluorescent signal either when an ether bond in the compound is broken by the thiol (—SH) group of cysteine or when an ether bond in the compound is broken by the thiol (—SH) group of cysteine and substituted with the amine (—NH$_2$) and thiol (—SH) of cysteine.

The thiol group in vivo refers to a form in which a sulfhydryl (—SH) group is attached to an alkyl or organic group, and in particular, a correlation between the thiol group in vivo and cancer has recently emerged. In particular, it has been reported that the thiol group of cysteine is highly correlated with cancer. For example, it has been reported that cysteine has the potential as a biomarker for malignant glioblastoma, a biomarker for diagnosis of prostate cancer, or a biomarker for breast cancer. However, a conventional method for detecting the thiol group in vivo has several obstacles, despite the importance of the thiol group.

When the compound of Formula 1 comes into contact with a sample containing cysteine and other biomolecules, it emits fluorescence by reaction with cysteine without reacting with other biomolecules. For example, the compound of Formula 1 may react only with cysteine in urine without reacting with other biomolecules in urine.

According to one embodiment of the present disclosure, the compound of Formula 1 may emit a higher intensity of fluorescent signal when reacting with a sample containing cysteine than when reacting a sample containing at least one selected from the group consisting of homocysteine, glutathione, and hydrogen sulfide.

According to one embodiment of the present disclosure, the compound of Formula 1 may emit a higher intensity of fluorescent signal when reacting with a sample containing cysteine than when reacting a sample containing at least one selected from the group consisting of homocysteine (e.g., DL-homocysteine), glutathione (e.g., L-glutathione), glutamine (e.g., L-glutamine), lysine (e.g., L-lysine), human serum albumin (HSA), PbCl$_2$, MGCl$_2$, FeCl$_3$, Hg(NO$_3$)$_2$, CdCl$_2$, ZnCl$_2$, NiCl$_2$, CoCl$_2$, NaCl, AuCl$_3$, AgCl, CuCl$_2$, and KCl.

The intensity of the fluorescence signal emitted when the compound of Formula 1 comes into contact with cysteine may be higher (e.g., more than one times higher, 5 times higher, 10 times higher, 20 times higher, 50 times higher, or 100 times higher) than the intensity of the fluorescent signal emitted when the compound comes into contact with other biomolecules, for example, at least one selected from the group consisting of homocysteine, glutathione, sodium sulfate, amino acids other than cysteine, homocysteine (e.g., DL-homocysteine), glutathione (e.g., L-glutathione), glutamine (e.g., L-glutamine), lysine (e.g., L-lysine), human serum albumin (HSA), PbCl$_2$, MGCl$_2$, FeCl$_3$, Hg(NO$_3$)$_2$, CdCl$_2$, ZnCl$_2$, NiCl$_2$, CoCl$_2$, NaCl, AuCl$_3$, AgCl, CuCl$_2$, and KCl. At this time, even if the upper limit of the intensity of the fluorescent signal is not specified, those skilled in the art can clearly understand the upper limit for the purpose of distinguishing between a case in which the compound does not come into contact with cysteine and a case in which the compound comes into contact with cysteine. However, for example, the upper limit may be, but is not limited to, 200 times or less, 150 times or less, 100 times or less, 50 times or less, 20 times or less, or 10 times or less.

For example, the compound of Formula 1 is capable of detecting cysteine in a sample containing at least one selected from the group consisting of biomolecules in urine. According to one aspect of the present disclosure, the biomolecules may be, but is not limited to, at least one selected from the group consisting of glutathione, aspartic acid, glutamine, lysine, arginine, adenosine triphosphate, sucrose, and ammonium.

When the compound of Formula 1 comes into contact with cysteine, it may emit fluorescence rapidly, for example, but not limited to, within 10 minutes, within 7 minutes, within 5 minutes, within 3 minutes, or within 1 minute.

According to the present disclosure, there is provided a composition for cysteine detection containing the compound represented by Formula 1 or a salt thereof.

The composition emits a fluorescent signal when bound to cysteine.

The composition may consist only of the compound of Formula 1 or a salt thereof, and may further contain other conventional components.

The composition may further contain a solvent selected from among water, methanol, ethanol, isopropanol, n-propanol, n-butanol, isobutanol, t-butanol, acetone, isopropyl ether, acetonitrile, diethyl ether, tert-butylmethyl ether, and mixtures thereof.

According to the present disclosure, there is provided a fluorescent probe including the composition for cysteine detection containing the compound represented by Formula 1 or a salt thereof.

The fluorescent probe according to an aspect of the present disclosure, which is a small organic molecule, may overcome problems caused by interference of other thiol groups. The fluorescent probe may emit a fluorescent signal when bound to cysteine, and thus detect the endoplasmic reticulum that is a cellular organelle. In addition, the fluorescent probe may display bright fluorescence in cells, such as cancer cells, which contain an increased level of cysteine due to a defense mechanism against reactive oxygen species, and thus it may be efficiently used for selective imaging and diagnosis of cancer cells or cancer tissue in cell or tissue biopsies. Furthermore, the fluorescent probe may be effectively used to diagnose brain tumor cells and brain tumor tissues in which cysteine is overexpressed, and to determine the prognosis of a brain tumor patient.

The field of fluorescent molecular probes has been developed extensively and used in many studies, because fluorescent molecular probes are conveniently used to visually observe various molecules, molecular activities, proteins, and protein activities in vivo. In particular, the fluorescent molecular probes have excellent utility for detecting metabolites in vivo with high sensitivity and specificity. In addition, since the fluorescent molecular probes facilitate the real-time observation of metabolites and proteins, the importance thereof is becoming more prominent.

Among fluorescent molecular probes that have been developed to date, a fluorescent molecular probe for selectively detecting cysteine, which is a thiol-type, has been difficult to develop. In addition, this fluorescent molecular probe was very complex structurally. The biggest reason why it is difficult to selectively detect cysteine is because of the problem caused by the structural similarity between cysteine and homocysteine (the number of carbon atoms in homocysteine—the number of carbon atoms in cysteine=1, that is, the difference in carbon atom number is 1).

In order to distinguish between cysteine and homocysteine, a structure having a low steric density, which is easily attacked by highly electrophilic and nucleophilic agents, had to be premised. In addition, to induce fluorescence, fluorescent molecular probes have been developed which use principles such as intramolecular charge transfer (ICT), Forster resonance energy transfer (FRET), photoinduced proton transfer (PET), or excited-state intramolecular proton transfer (ESIPT).

Typically, fluorescent molecular probes for detecting metabolites in vivo are designed with fluorescence turn-on, fluorescence turn-off, and fluorescence change systems. Among them, the fluorescent molecular probe of the fluorescence turn-on system is characterized in that it has a high resolution and sensitivity with a lower error potential in vivo than the fluorescence turn-off system. In addition, the fluorescence turn-on system can help stable imaging in real-time imaging in vivo with a higher resolution than the fluorescence change system.

For this reason, the development of a cysteine detection fluorescent probe with the fluorescence turn-on system still remains a very challenging task despite the importance thereof. According to the present disclosure, a cysteine detection fluorescent probe with this system is provided, which enables early diagnosis of cancer and can contribute to overcoming cancer.

That is, the composition may be used for cancer diagnosis. For example, the composition may be used for the diagnosis of brain tumors and for the diagnosis of glioblastoma. As described above, the compound of Formula 1 or the composition containing the same can detect an increased level of cysteine than that in normal tissues by the intensity of fluorescence.

As a result, the compound represented by Formula 1 or the composition containing the same may be used in a method for providing information for diagnosing cancer, the method including a step of treating a sample with the compound represented by Formula 1 or a salt thereof.

The cancer may be brain tumor, bladder cancer, bone cancer, brain cancer, breast cancer, central nervous system cancer, adrenal cancer, placental cancer, testicular cancer, cervical cancer, colon cancer, kidney cancer, head and neck cancer, pituitary cancer, myeloma, leukemia, liver cancer, lung cancer, pancreatic and biliary tract cancer, melanoma, ovarian cancer, pancreatic cancer, prostate cancer, skin cancer, stomach cancer, thyroid cancer, uterine cancer, carcinoma, lymphoma, sarcoma, eye cancer, esophageal cancer, bile duct cancer, or vulvar cancer.

According to one embodiment of the present disclosure, the composition may be used for diagnosing cervical cancer. In examples of the present disclosure, the compound represented by Formula 1 was synthesized by a method capable of mass synthesis, and whether the synthesized compound is capable of early diagnosing cancer by detecting cysteine in urine was examined. As a result, it was confirmed that a high fluorescence turn-on signal was observed in urine a cervical cancer patient group. In addition, it was confirmed that the fluorescence turn-on signal was caused by cysteine, not by homocysteine having a similar structure. That is, the fluorescent probe of the present disclosure is capable of detecting cysteine in urine, and thus may be used to diagnose cancer in a cervical cancer patient group.

According to the present disclosure, there is provided a method for detecting cysteine, the method including steps of: bringing a composition containing the compound represented by Formula 1 or a salt thereof into contact with a sample containing cysteine; and checking fluorescence.

When a sample containing cells is treated with the compound of Formula 1, the compound may show a fluorescence turn-on property in the intracellular endoplasmic reticulum.

For example, a compound including a structure of 4-nitro-7-(perfluorophenoxy)benzo[c][1,2,5]oxadiazole may undergo a Smiles rearrangement by reaction with cysteine, and attack the amine group (—$NH_2$) and thiol group (—SH) of the cysteine, thus exhibiting a fluorescence turn-on property.

The sample may be a biological sample. The biological sample may be, but is not limited to, body fluid, urine, saliva, blood, cerebrospinal fluid, or the like.

According to one embodiment of the present disclosure, the body fluid may be urine. Urine is the first human body fluid tested for disease diagnosis, and has been used to date as a diagnostic sample in a wide range of fields for diagnosis of kidney disease, metabolic disease, cancer, and infection. To date, various urine biomarkers such as thrombin, microRNA (miRNA), DNA, and reactive oxygen species (ROSs) have been discovered. Since these biomarkers have a concentration of $10^{-13}$ M to $10^{-1}$ M, error for a sample may increase during analysis performed through a complex process. Therefore, there is a need to develop systems capable of detecting biomarkers at several nanomolar concentrations.

According to one embodiment of the present disclosure, the compound of Formula 1 is capable of detecting a trace amount of cysteine contained in urine. For example, it is capable of detecting 10 ng/μL or less, 5 ng/μL or less, or 1 ng/μL or less of cysteine, and thus has high cysteine detection sensitivity. At this time, even if the upper limit and lower limit of the concentration of cysteine contained in urine, which may be detected by the compound for cysteine detection according to one embodiment of the present disclosure, are not specified, the upper limit and lower limit can be clearly understood by those skilled in the art. For example, the lower limit of the concentration of cysteine in urine, which may be detected by the compound according to one embodiment of the present disclosure, may be higher than 0 ng/μL.

Figure 1A:
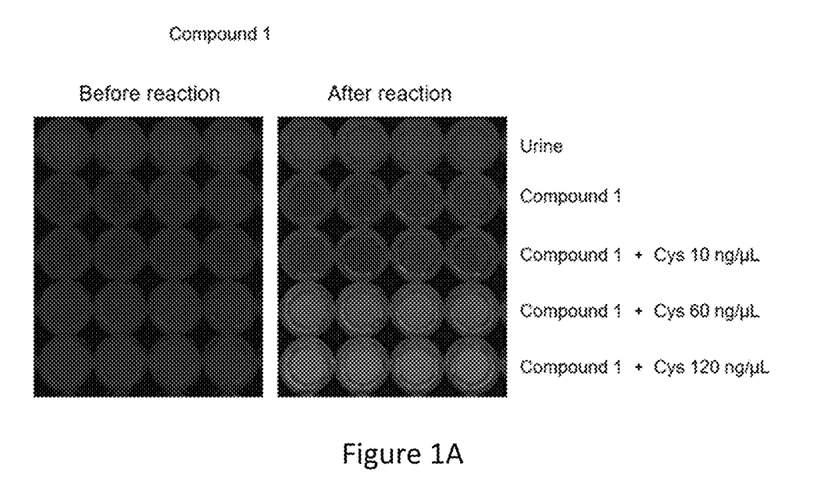
FIGS. 1A and 1B show fluorescence photographs of Compound 1 in a 365-nm UV chamber and a graph showing the results of measuring the fluorescence intensity (emission spectrum) upon excitation at 488 nm, respectively, in accordance with embodiments of the present disclosure.

Referring to FIG. 1(a), it can be seen that, when the compound of Formula 1 contacts and reacts with cysteine in urine, it emits fluorescence and the intensity of the fluorescence increases as the concentration of cysteine increases. In addition, referring to FIG. 1(b), it can be confirmed that this characteristic appears even when the compound of Formula 1 reacts with a very low concentration of cysteine.

Figure 2A:
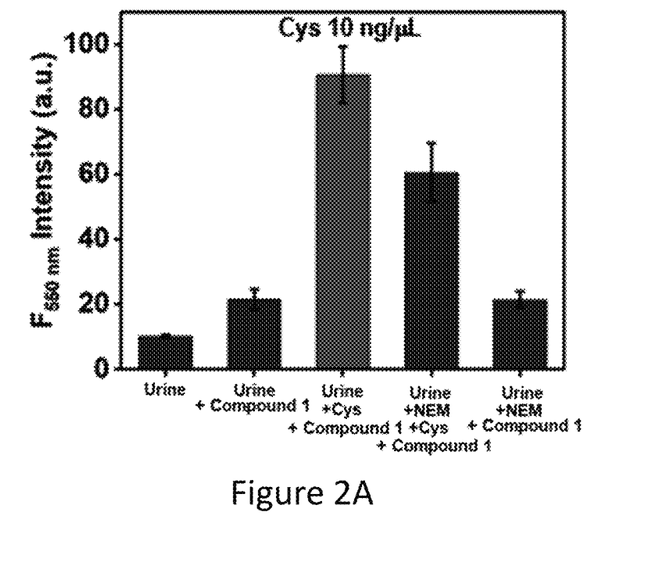
FIGS. 2A and 2B show the results of evaluating the reactivity and selectivity of Compound 1 to cysteine by measuring the fluorescence intensity after reaction therebetween, in accordance with embodiments of the present disclosure.
Figure 2B:
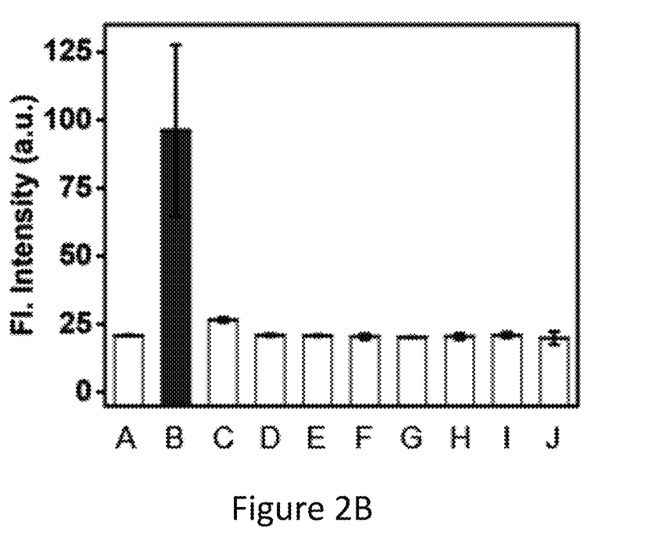

FIGS. 2(a) and 2(b) show the fluorescence intensities obtained when the compound of Formula 1 reacted with biomolecules including cysteine in urine, and as can be seen therein, only cysteine shows a significant fluorescence intensity value.

Figure 4:
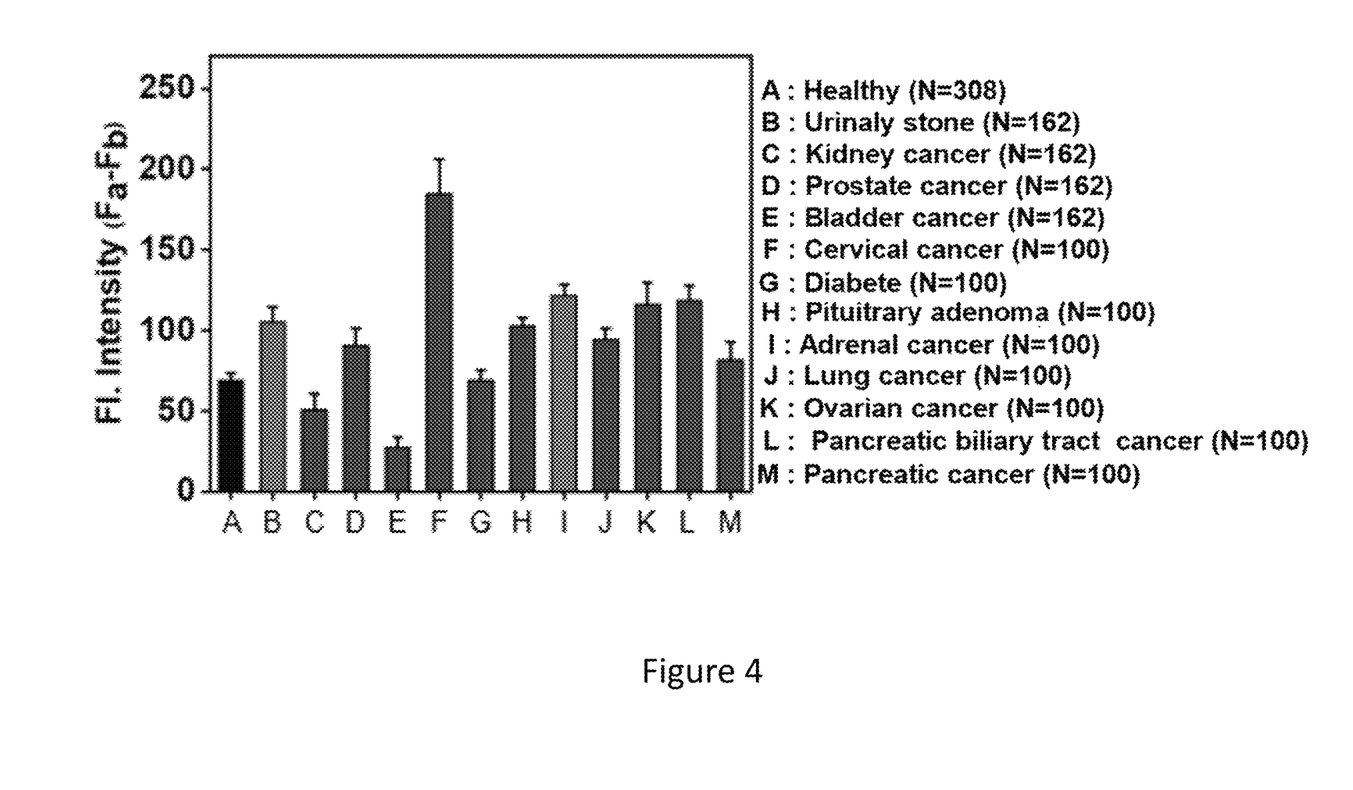
FIG. 4 shows the results of evaluating the reactivity of Compound 1 with the urine collected from various patient groups by measuring the fluorescence intensity after reaction therebetween, in accordance with embodiments of the present disclosure.

According to one embodiment of the present disclosure, the compound of Formula 1 shows fluorescence turn-on by reaction with cysteine in urine. As fluorescence turn-on occurs in patient groups with urolithiasis, cervical cancer, adrenal cancer, ovarian cancer, and pancreatic and biliary tract cancer, unlike a normal group, cysteine may exist in the urines of the patient groups and may be detected by the compound of Formula 1.

It can be seen that the occurrence of fluorescence turn-on by the compound of Formula 1 in the urine of a cervical cancer patient is not attributable to the body mass index (BMI) of the cervical cancer patient group, and the concentration of lipids in the urine does not interfere with the detection of cysteine.

According to the present disclosure, there is provided a method for producing the compound represented by Formula 1, the method including a step of allowing a compound represented by the following Formula 2 to react with a compound represented by the following Formula 3:

[Formula 2]

[Formula 3]

wherein: $X_1$ to $X_5$ are each independently hydrogen, deuterium, halogen, or a (C1-C6) alkyl group; at least one of $X_1$ to $X_5$ is a halogen; Hal is a halogen; and Y is hydrogen, a (C1-C6) alkyl group, a (C2-C6) alkenyl group, a (C2-C6) alkynyl group, a (C1-C6) alkoxy group, a hydroxyl group, a hydroxyethyl group, an alkylamino group, a nitro group, a sulfonyl group, a sulfinyl group, a carboxyl group, a acetoxy group, a phenyl group, a (C7-C13) alkylphenyl group, a (C7-C13) alkylphenyloxy group, a (C8-C13) alkynylphenyl group, a (C8-C13) alkenylphenyl group, or a phenoxy group.

According to the present disclosure, the method may include, for example, a step of allowing 4-chloro-7-nitrobenzofurazan to react with pentafluorophenol, thus producing a compound including a structure of 4-nitro-7-(perfluorophenoxy)benzo[c][1,2,5]oxadiazole.

In the production method, the halogen in Formulas 1 to 3 may be a fluoro group, a chloro group, a bromo group, an iodo group, or the like.

According to one embodiment of the present disclosure, $X_1$ to $X_5$ in Formula 1 may be each a fluoro group.

According to one embodiment of the present disclosure, Y in Formula 1 may be a nitro group.

The production method may further include a step of adding N,N-diisopropylethylamine (DIPEA).

Hereinafter, the present disclosure will be described in more detail with reference to the following examples. However, these examples are only illustrative of the present disclosure, and the scope of the present disclosure is not limited by these examples.

Example 1. Synthesis and Structural Analysis of Composition for Detecting Cysteine in Urine In order to develop a fluorescent molecular probe for rapidly detecting cysteine in urine derived from a living body, the present inventors have designed a molecular structure by introducing the aromatic ring compound pentafluorophenol, which lacks electrons, to 4-chloro-7-nitrobenzofurazan so as to facilitate nucleophilic attack. Synthesized compound 1 does not show fluorescence due to the presence of a nitrogen dioxide ($NO_2$) group that attracts electrons and pentafluorophenol that attracts electrons at the para position thereof, but when it binds to cysteine and the electron-donating amine group ($NH_2$) of cysteine is introduced at the para position, fluorescence turn-on is observed near 550 nm. Based on the hypothesis that when the aromatic ring compound that lacks electrons is present, fluorescence turn-on will occur only in cysteine without interference of other thiol group-containing amino acids such as homocysteine and glutathione, the present inventors have devised Compound 1 and synthesized Compound 1 according to the following reaction scheme.

(1) Synthesis of 4-nitro-7-(Perfluorophenoxy)benzo [c][1,2,5]oxadiazole) (Compound 1)

Specifically, 4-chloro-7-nitrobenzofurazan (200 mg, 0.001 mol, TCI, A55921G) and pentafluorophenol (552 mg, 0.003 mol, TCI, 771-61-9) as synthetic starting materials were dissolved in 30 mL of N,N-dimethylformamide (DMF) deoxygenated with nitrogen, and the solution was stirred at a speed of 300 rpm and at 25° C. Thereafter, 300 µL of N,N-diisopropylethylamine (DIPEA) and 207 mg of potassium carbonate ($K_2CO_3$) were added thereto, and the temperature was raised to 60° C. on a silicone oil container. When the temperature reached 60° C., the mixture was stirred for 10 minutes, and then the temperature was lowered to 25° C. and the reaction was stopped with water (30 mL). In order to extract the organic layer, ethyl acetate (EtOAc) and water were mixed together at a ratio of 1:1 and added to the reaction solution through a separatory funnel, and only the organic layer could be separately obtained through this process. Thereafter, the organic layer was dried over anhydrous sodium sulfate ($Na_2SO_4$, 2 g) and concentrated using a rotary evaporator at 37° C. and 20 to 500 mmHg. The dark brown solid compound thus obtained was separated by column chromatography (diameter: 6 cm, height: 15 cm) using silica gel (Merck-silica gel 60, 230 to 400 mesh) (eluent: EtOAc/hexane=10/90) to obtain a dark yellow solid compound (110.2 mg, 31.75% yield).

Nuclear magnetic resonance (NMR) analysis was performed to confirm whether the synthesis would be successfully performed. Through the analysis, it could be confirmed that compound 1 was successfully synthesized. The results of the NMR analysis are as follows.

(2) Results of NMR Results $^1$H NMR ($CDCl_3$, 400 MHz, 298.2 K): δ 8.50 (d, 1H, J=8.06 Hz), 6.83 (d, 1H, J=8.30 Hz). $^{13}$C NMR ($CDCl_3$, 400 MHz, 294.2 K): δ 109.41, 127.39, 128.79, 130.96 131.45, 132.31, 132.66, 137.14, 140.14, 141.73, 142.67, 144.09, 150.70. $^{19}$F NMR (hexafluoro-benzene, 500 MHz): δ −155.7493 (d, 2F), −157.9279 (t, 1F), −162.5784 (t, 2F).

Example 2. Analysis of Fluorescence Emission Characteristics

In order to confirm the reaction of Compound 1 with cysteine in urine, non-pretreated urine (198 µL) was treated with varying concentrations (1 to 120 ng/µL) of cysteine, and then treated with Compound 1 (100 µM). The resulting urines were stirred in a stirrer at 37° C. for 40 minutes, and the fluorescence spectra were measured (excitation wavelength: 488 nm). In addition, Compound 1 was used after dissolution in a DMSO solution at 10 mM, and the amount of DMSO in the final solvent condition was controlled to be the same for each container (less than 1%).

Specifically, a spectro-fluorophotometer (SHIMADZU Corp. RF-6000, Japan) was used to analyze the emission spectrum, and the glass cuvette used for fluorescence measurement was a standard quartz cell (internal volume=0.1 cm, Hellma Analytics, Jena, Germany) having a thickness of 1 cm on all sides. In addition, a chamber (WUV-L10, DAIHAN Scientific) capable of excitation at a wavelength of 365 nm was used to visually observe the fluorescence change.

Figure 1B:
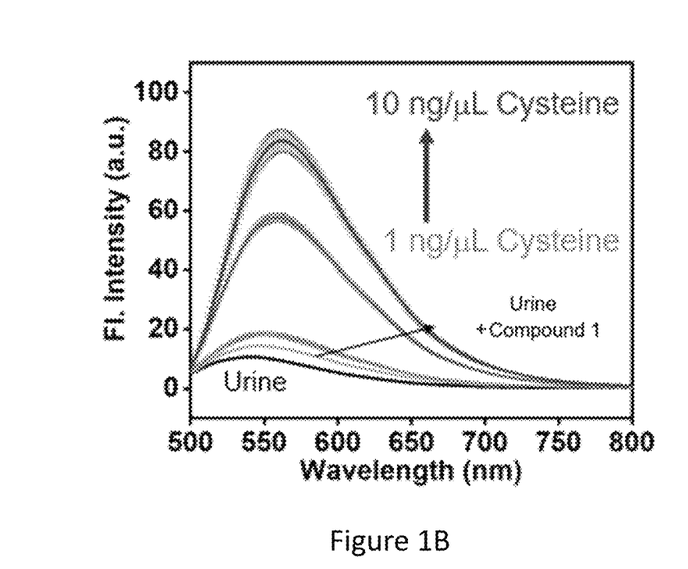

FIG. 1(*a*) shows an image obtained for normal urine treated with Compound 1 (100 µM), and images obtained for normal urine which was treated with cysteine (10 to 120 ng/µL), then treated with compound 1 (100 µM), and then stirred in a stirrer at 37° C. for 40 minutes, followed by excitation at 365 nm. When the urine was treated with compound 1 (100 µM) and cysteine (60 ng/µL or higher), fluorescence changes were visible without a separate fluorescence measurement device. Although fluorescence changes were not visible when the urine was treated with Compound 1 (100 µM) and cysteine (concentration of 10 ng/µL or lower), examination was made as to whether fluorescence changes in this treatment could be confirmed using a fluorescence measurement device (FIG. 1(*b*)). Referring to FIG. 1(*b*), significant fluorescence changes could be obtained in the presence of 1 ng/µL of cysteine in urine, and statistical data thereon are shown below. The fluorescence spectra in FIG. 1(*b*) showed the highest fluorescence value at 550 nm or more and 600 nm or less.

Example 3. Analysis of Binding Selectivity of Compound 1 to Cysteine

The present inventors analyzed the binding selectivity of Compound 1 to cysteine in urine through fluorescence changes, and the results of the analysis are shown in FIGS. 2(*a*) and 2(*b*).

Specifically, in order to determine whether Compound 1 selectively binds to cysteine in urine, cysteine and N-ethylmaleimide (NEM) (500 µM) capable of lowering cysteine concentration in urine were used. In addition, glutathione, aspartic acid, glutamine, lysine, arginine, adenosine triphosphate, sucrose, and ammonium used in the experiment were products obtained from TCI (Tokyo Chemical Industry Co., Ltd), Sigma Aldrich, and Alfa Company. The concentration of each biomolecule was equally measured at 100 µM. In addition, in order to obtain fluorescence spectra and values, Compound 1 and an unknown sample were stirred at 37° C. for 40 minutes and then excited at a wavelength of 488 nm.

In FIG. 2(a), it was confirmed that Compound 1 showed a high fluorescence value in the urine containing cysteine, but the fluorescence value decreased in the group co-treated with Compound 1 and N-ethylmaleimide which reduces cysteine, suggesting that Compound 1 binds to cysteine in urine, thus inducing fluorescence turn-on. In addition, as a result of examining whether Compound 1 can bind to biomolecules detectable in urine, as shown in FIG. 2(b), a significant fluorescence change could be observed only for cysteine in urine. The types of biomolecules indicated on the x-axis of FIG. 2(b) are as follows, and the following Probe 1 corresponds to Compound 1:

(A) Probe 1;
(B) Probe 1 with L-cysteine;
(C) Probe 1 with L-glutathione;
(D) Probe 1 with L-aspartic acid;
(E) Probe 1 with L-glutamine;
(F) Probe 1 with L-lysine;
(G) Probe 1 with L-arginine;
(H) Probe 1 with adenosine triphosphate;
(I) Probe 1 with sucrose;
(J) Probe 1 with ammonium.

Example 4. Fluorescence Spectral Analysis of Compound 1 in Urine Derived from Cervical Cancer Patient The present inventors performed fluorescence spectral analysis to confirm whether Compound 1 would show significant fluorescence changes in urines derived from cervical cancer patients, and the results of the analysis are shown in FIGS. 3(a) and 3(b).

Figure 3A:
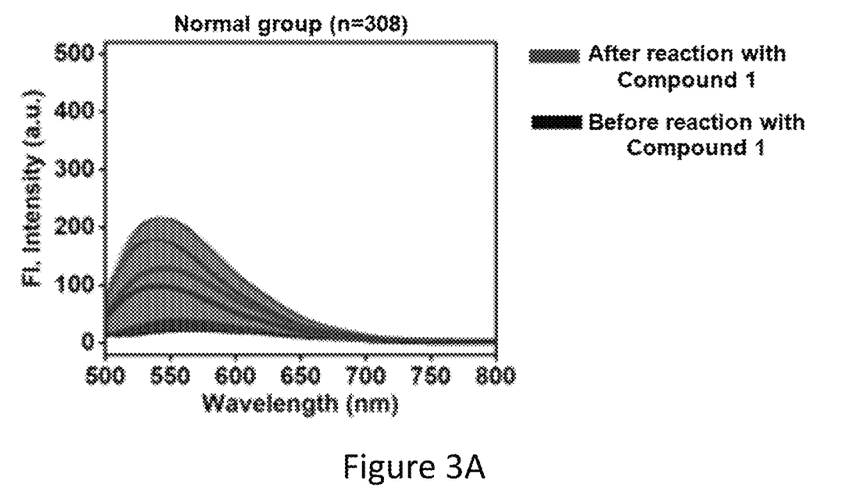
FIGS. 3A and 3B show the results of evaluating the reactivity of Compound 1 with the urine collected from a normal group (n=308) or a cervical cancer patient group (n=100) by measuring the fluorescence intensity after reaction therebetween, in accordance with embodiments of the present disclosure.

More specifically, FIG. 3(a) is a graph showing the results of examining whether Compound 1 (100 µM) shows fluorescence changes in urines (N=308) derived from humans without disease. Specifically, fluorescence spectral analysis was performed immediately after treatment of the urines with Compound 1 (black line). After stirring at 37° C. for 40 minutes, fluorescence spectral analysis was performed (red line). FIG. 3(b), in contrast, is a graph showing the results of examining whether Compound 1 (100 µM) shows fluorescence changes in urines (N=100) derived from cervical cancer patients. Specifically, fluorescence spectral analysis was performed immediately after treatment of the urines with Compound 1 (black line). After stirring at 37° C. for 40 minutes, fluorescence spectral analysis was performed (red line).

Figure 3B:
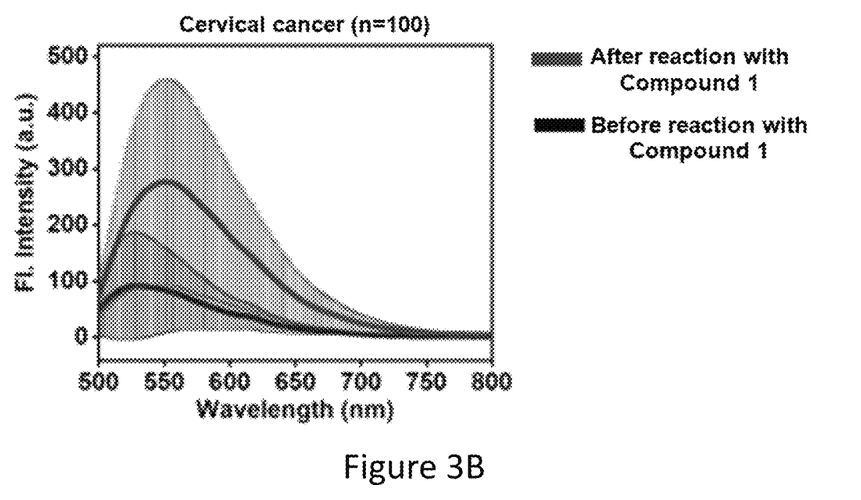

Through FIGS. 3(a) and 3(b), it was confirmed that Compound 1 showed high fluorescence values after reaction in the urines derived from cervical cancer patients, suggesting that cysteine in the urines derived from cervical cancer patients may be more than that in the normal group. In addition, these results suggest that a patient with cervical cancer can be diagnosed with urine using Compound 1.

Example 5. Fluorescence Spectral Analysis of Compound 1 in Urines Derived from Patients with Other Diseases Including Cancer The present inventors performed fluorescence spectral analysis to confirm whether Compound 1 shows significant fluorescence changes in urines derived from patients with cancers other than cervical cancer or other diseases. In addition, the results of the analysis are shown in FIG. 4.

The graph of FIG. 4 shows the results obtained by treating urines, collected from patients with cervical, patients with other cancers and patients with other diseases, with Compound 1, and analyzing the difference in fluorescence intensity between before and after the treatment to confirm whether Compound 1 shows significant fluorescence intensity.

The urines used in the experiment were collected from urolithiasis patients (B, N=162), kidney cancer patients (C, N=162), prostate cancer patients (D, N=162), bladder cancer patients (E, N=162), cervical cancer patients (F, N=100), diabetic patients (G, N=100), pituitary cancer patients (H, N=100), adrenal cancer patients (I, N=100), lung cancer patients (J, N=100), ovarian cancer patients (K, N=100), pancreatic and biliary tract cancer patients (L, N=100), and pancreatic cancer patients (M, N=100). In the measurement method, each of the collected urine (198 µL) and Compound 1 (100 µM) were mixed together, the fluorescence spectra thereof were measured, and the highest fluorescence intensity value was taken. Then, each mixture was stirred at 37° C. for 40 minutes, and the highest fluorescence intensity value obtained from the fluorescence spectra was taken. The difference between the fluorescence intensity values before and after the reaction was shown as a bar graph.

As a result, it was confirmed that, in the case of urolithiasis patients (B), cervical cancer patients (F), adrenal cancer patients (I), ovarian cancer patients (K) and pancreatic and biliary tract cancer patients (L), noticeable fluorescence emission was observed. In particular, it could be confirmed that this effect was the greatest in the case of cervical cancer patients (F).

The use of the 4-nitro-7-(perfluorophenoxy)benzo[c][1,2,5]oxadiazole compound could selectively detect cysteine in urine without interference of other biomolecules.

It is considered that the present disclosure stands out for its innovativeness and creativity in that it is the first material that is practical in both biological and molecular diagnostic fields.

In particular, urines from various cancer patients were screened and analyzed using Compound 1, thereby sufficiently demonstrating the possibility of Compound 1 for early diagnosis of a specific cancer type. Among the cancer patient urines screened, the most significant value could be obtained, especially in the cervical cancer patient urines, and these study results sufficiently suggest that the immediate commercialization of the compound of the present disclosure is possible and the future commercialization prospect of the technology of the present disclosure is clear.

In addition, since the compound of the present disclosure focuses on metabolites that are difficult to access in the field of molecular diagnostics, it is endowed with high technological innovation in that it can quickly detect metabolites that are difficult to detect by conventional molecular diagnostic methods, for example, polymerase chain reaction (PCR) and Western blotting.

As described above, the fluorescent probe according to the present disclosure is a small organic molecule, may emit a fluorescent signal when bound to cysteine, and thus overcomes a problem with a conventional fluorescent probe having a complex structure for detecting cysteine and a problem caused by interference between cysteine and other thiol groups.

In addition, the fluorescent probe of the present disclosure may detect the endoplasmic reticulum, which is an organelle, and may display bright fluorescence in cells, such as cancer cells, which contain an increased level of cysteine due to a defense mechanism against reactive oxygen species. Thus, it may be efficiently used for selective imaging and diagnosis of cancer cells or cancer tissue in cell or tissue biopsies.

Furthermore, the fluorescent probe may be effectively used to diagnose brain tumor cells and brain tumor tissues in which cysteine is overexpressed, and to determine the prognosis of a brain tumor patient.

Accordingly, the fluorescent probe of the present disclosure may be applied in various research fields such as cysteine-related intracellular mechanism research, cysteine-related cancer mechanism research, cysteine-related therapeutic agent development, and therapeutic agent efficacy research.

In addition, since the fluorescent probe of the present disclosure has low cytotoxicity and in vivo toxicity, it not only has a wide range of biological applications, but also enables cancer imaging through intravenous injection thereof, in particular, brain tumor imaging because it can pass through the blood vessel wall of the brain.

Since the fluorescent probe of the present disclosure selectively shows a high fluorescence signal even in a human brain tumor tissue sample, it may also be applied to image-based surgery.

Accordingly, the present disclosure is expected to be widely used in basic science and clinical research fields.

The foregoing description of the embodiments of the invention has been presented for the purposes of illustration and description. It is not intended to be exhaustive or to limit the invention to the precise form disclosed. Many modifications and variations are possible in light of this disclosure.

It is intended that the scope of the invention be limited not by this detailed description, but rather by the claims appended hereto.

What is claimed is:

1. A method for providing information for diagnosing cancer, the method comprising a step of treating a urine sample with a compound represented by the following Formula 1 or a salt thereof:

[Formula 1]

wherein:
$X_1$ to $X_5$ are each a fluoro group; and
Y is a nitro group.

2. The method of claim 1, wherein the cancer is cervical cancer.

3. The method of claim 1, wherein 1 ng/µL or less of cysteine is detected.

* * * * *